US011779253B1

(12) United States Patent
Chi

(10) Patent No.: US 11,779,253 B1
(45) Date of Patent: Oct. 10, 2023

(54) MEASUREMENT OF ELECTRODE IMPEDANCES IN BIOPOTENTIAL-PHYSIOLOGICAL-PHENOMENA SENSING SYSTEMS

(71) Applicant: Yu Mike Chi, San Diego, CA (US)

(72) Inventor: Yu Mike Chi, San Diego, CA (US)

(73) Assignee: COGNIONICS, INC., San Diego, CA (US)

( * ) Notice: Subject to any disclaimer, the term of this patent is extended or adjusted under 35 U.S.C. 154(b) by 1017 days.

(21) Appl. No.: 16/665,860

(22) Filed: Oct. 28, 2019

(51) Int. Cl.
*A61B 5/30* (2021.01)

(52) U.S. Cl.
CPC .................................... *A61B 5/30* (2021.01)

(58) Field of Classification Search
CPC ......... A61B 5/291; A61B 5/296; A61B 5/297; A61B 5/30; A61B 5/301; A61B 5/308; A61B 5/31; A61B 5/37; A61B 5/384; A61B 5/389
See application file for complete search history.

(56) References Cited

U.S. PATENT DOCUMENTS 5,792,063 A * 8/1998 Danielsson ............ A61B 5/276 600/509
6,487,449 B1 * 11/2002 Kaiser .................... A61B 5/276 607/28
8,086,300 B2 * 12/2011 Herlerkson ............ A61B 5/301 600/509
10,383,537 B2 * 8/2019 Li .......................... A61B 5/282
2002/0046756 A1 * 4/2002 Laizzo ................. A61N 1/0573 128/899
2006/0020218 A1 * 1/2006 Freeman .................. A61B 5/24 600/509
2007/0038257 A1 * 2/2007 Gray ...................... A61B 5/276 607/8
2014/0088394 A1 * 3/2014 Sunderland .......... A61B 5/6843 600/373
2017/0135640 A1 * 5/2017 Gunasekar ............. A61B 5/291
2019/0274568 A1 * 9/2019 Shahdoostfard ....... A61B 5/339
2021/0290952 A1 * 9/2021 Sunderland .............. A61N 1/08

* cited by examiner

*Primary Examiner* — Jacqueline Cheng
*Assistant Examiner* — Tho Q Tran
(74) *Attorney, Agent, or Firm* — Edward W. Callan

(57) ABSTRACT

In a biopotential-physiological-phenomena sensing system, an impedance measurement circuit for measuring the impedance of a channel electrode that is applied to a subject's body for sensing a physiological phenomenon includes: an amplifier, a DC-biased power supply with an AC component and a conductive element. The amplifier has a signal input coupled to a channel electrode that is applied to a subject's body and a signal output for providing an output voltage that is representative of a voltage provided at the signal input in accordance with an amplification of the amplifier. The conductive element is coupled between the power supply and the signal input of the amplifier. The AC component of the DC-biased power supply causes a known test current to flow through the channel electrode thereby causing a voltage drop proportional to the impedance of the channel electrode at the input of the amplifier. The impedance of the channel electrode is measured in accordance with the amplifier's output voltage.

7 Claims, 2 Drawing Sheets

100
110
$i_s$
$Z_s$
108
$V_s$
102
$V_+$
104
106
$i_s$
$V_{body}$
$Z_e$
in
out
$V_{out}$
$V_{dc}$
$V_-$
101
$i_s$
$Z_g$
112
116
$V_+$
118
114
$Z_r$
in
out
$V_{ref}$
$V_{dc}$
$V_-$

MEASUREMENT OF ELECTRODE IMPEDANCES IN BIOPOTENTIAL-PHYSIOLOGICAL-PHENOMENA SENSING SYSTEMS

BACKGROUND OF THE INVENTION

This invention generally relates to measurement of electrode impedances in biopotential acquisition systems, such as ECG, EEG or EMG systems, and is specifically directed to an improved system for making such a measurement.

In a biopotential acquisition system, it is often desirable to measure the impedance of an electrode that is used to connect the acquisition system to the body of a subject. Electrode impedance values allow for the determination of both system failure (e.g., electrodes have fallen off) and signal quality (e.g., impedance is too high resulting in extra noise). An impedance monitoring feature is especially critical in higher density applications (e.g., EEG systems and 12-lead ECG systems) in order to assist the user in proper alignment and maintenance of the electrodes to ensure optimum recordings.

Virtually all impedance measurement techniques rely on utilizing Ohms's law, V=IR (or its AC equivalent V=IZ) by causing a known test current to flow through the impedance and then measuring the resultant voltage across the impedance. For purposes of simplicity, the terms resistance and impedance (as well as their inverse characteristics of conductance and admittance) are used interchangeably unless specifically noted.

SUMMARY OF THE INVENTION

The invention provides an electrode impedance measurement circuit in a biopotential-physiological-phenomena sensing system for measuring the impedance of a channel electrode that is applied to a subject's body for sensing said physiological phenomenon, the circuit comprising: an amplifier having a signal input coupled to a channel electrode that is applied to a subject's body and a signal output for providing an output voltage that is representative of a voltage provided at the signal input in accordance with an amplification of the amplifier; a DC-biased power supply with an AC component connected to the power supply terminal of said amplifier; and a conductive element coupled between the power supply and the signal input of the amplifier; wherein the AC component of the power supply generates and modulates a known test current from the conductive element and thence from the signal input of the amplifier through a said channel electrode that is applied to a subject's body to produce a said output voltage from the amplifier that is representative of a voltage provided at the signal input in accordance with an amplification of the amplifier.

In a biopotential-physiological-phenomena sensing system having multiple measurement channels respectively including an electrode in each channel that is applied to a subject's body for sensing a said physiological phenomenon, a plurality of impedance measurement circuits for respectively measuring the impedance of the channel electrode in at least some of the measurement channels, a plurality of the above-described impedance measurement circuits are included for respectively measuring the impedance of the channel electrode in at least some of the measurement channels.

DETAILED DESCRIPTION

Figure 1:
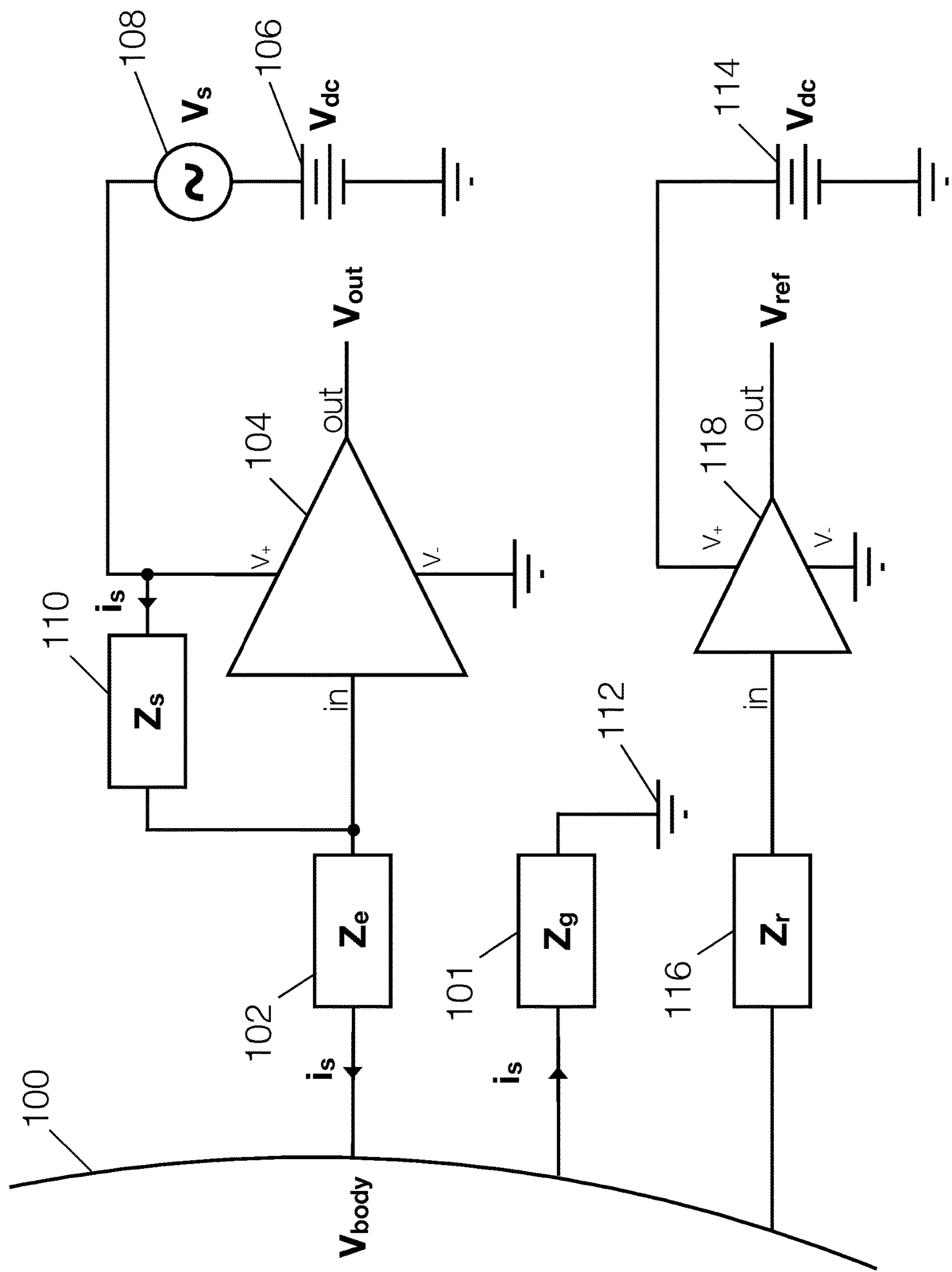
FIG. 1 is a schematic diagram showing a first exemplary embodiment of the impedance measurement circuit of the invention wherein the conductive element that converts the AC component of the DC-biased power supply is a discrete element.

Referring to FIG. 1, a first exemplary embodiment of the impedance measurement circuit of the invention for measuring the impedance Ze of a channel electrode 102 in a single individual measurement channel includes an amplifier 104, a DC biased power supply with an AC component 106, 108, and a conductive element 110 having an impedance Zs. Note, in the embodiments shown herein, the figures of the Drawing illustrate only a single channel. Without loss of generality, the concept can be extended to an arbitrarily large sensor array by replicating the single channel structure for each channel where an impedance check functionality is desired. The impedance measurement function also involves the body 100 to which a channel electrode 102 having impedance Ze is attached. The channel electrode 102 is connected to the input of the amplifier 104. The amplifier 104 preferably has an input impedance substantially higher than the impedance Ze of the channel electrode 102 and a voltage gain of unity (e.g., voltage follower). With an amplifier 104 having some other gain specification, the output Vout is scaled appropriately to adjust for the gain introduced by the amplifier 104.

The amplifier 104 preferably has an input impedance substantially higher than the impedance Ze of the channel electrode 102 and a voltage gain of unity (e.g., voltage follower). With an amplifier 104 having some other gain specification, the output Vout is scaled appropriately to adjust for the gain introduced by the amplifier 104.

In the exemplary embodiment of FIG. 1, the amplifier 104 is a Texas Instruments OPA376 operational amplifier, which is preferred because of its low input noise and high input impedance, making it well suited for EEG applications. Other embodiments may utilize a different amplifier, depending on the needs (e.g., bandwidth, power, noise) of the specific use.

The voltage applied to the power supply terminals of the amplifier 104 by the DC biased source with an AC component 106, 108 can be decomposed into two parts: a DC bias provided by a DC voltage source 106 having a nominal voltage of Vdc and an AC voltage source 108 providing a time varying signal Vs. In practice, the power supply is one source, having a combined DC and AC component, but for purposes of illustration it is helpful to schematically decompose the power supply into the static DC 106 and time varying AC 108 components to better understand the operation of the circuit. In the embodiment of FIG. 1, the DC voltage source 106 supply is set to 2.7V, and the AC voltage source 108 provides a triangular wave of 300 mV peak-to-peak at 125 Hz; which allows the minimum supplied voltage (2.7V−0.15V=2.55V) to still fall within the specified required range for an OPA376 operational amplifier 104. The frequency of 125 Hz was chosen since it falls outside of the typical EEG bandwidth. Other embodiments of the invention may choose to utilize different power supply voltages and AC frequencies, depending on the requirements of the phenomena sensing application.

Note that the illustrated embodiment, the voltage output from the power supply 106, 108 is applied to the positive power input terminal of the amplifier 104 for ease of illustration. Without loss of generality, other embodiments may modulate the negative power input terminal of the amplifier 104 in applications wherein the positive input terminal is used as the circuit 'neutral' node. In other embodiments, the voltage output from the power source 106, 108 may be applied across both the positive and negative amplification input terminals of the amplifier 104 in a bipolar power supply design where the 'neutral' node of the circuit is independent from the positive and negative power supply terminals of the amplifier 104.

A ground electrode 101 having an impedance Zg connects the subject's body to circuit ground 112 (or other neutral potential, or right leg drive) of the amplifier circuit through a ground electrode 101 having impedance Zg. Once again, the ground electrode 101 is connected back to the negative supply of the amplifier only for purposes of illustration and clarity. Since impedance check is a time varying AC signal, the ground electrode 101 can be connected to any virtual ground or neutral potential (or right leg drive) necessary to bias the potential of the body for optimal operation of the amplifier 104 in the circuit.

A conductive element 110 having an impedance Zs is connected between the positive power supply of the amplifier 104 back to the input of the amplifier 104. The impedance Zs may be a resistor, capacitor, inductor or any arbitrary series-parallel combination thereof. In practice, however, the conductive element 110 at least contains a series blocking capacitor so as to avoid the flow of DC currents into the body. A resistor could be used as the conductive element 110, but such will allow for potentially harmful DC currents, due to the DC-bias portion of the power supply 106. Also, a resistor may be lower in impedance than a capacitor at the frequencies of interest for physiological recordings, which is generally undesirable. However, a resistor may be useful in some designs since it biases the input of the amplifier 104 to a known voltage should the channel electrode 102 become disconnected. Inductors are generally not useful for physiological recordings, due to their low impedance at the frequencies used in surface electrophysiological recordings, but may be useful for higher frequency applications of this technique.

In the embodiment of FIG. 1, the conductive element 110 is a 10 pF capacitor. A small capacitor minimally degrades the input impedance of the amplifier and also blocks potentially harmful DC current flow. Other embodiments may choose to utilize different components depending on the needs of the application, as discussed above.

The AC component of the power supply 108 applies an excitation signal Vs that causes a test current, is, to flow out of the power supply 108 through the conductive element 110, into the channel electrode 102, through the body 100 and exit via the ground electrode 101 and returning to the circuit ground 112. By inspection, it can be seen that the value of the test current is: is =Vs/(Zs+Ze+Zg), where each of the quantities are complex numbers representing both magnitude and phase. Note Vdc is zeroed in the above equation by linear superposition since the impedance check is conducted in the AC (e.g., time varying) domain.

Although this technique will function with any conductive element value of Zs, it is usually desirable for physiological sensors to maintain a very high input impedance such that the signal from the body is invariant to changes in the impedance of the channel electrode 102. This can be accomplished easily by using a small capacitor for the conductive element 110, which also has the additional benefit of limiting potential currents to values far below the threshold considered to be dangerous.

Provided that the impedance Zs of the conductive element 110 is significantly higher than the impedance Ze of the channel electrode 102 and ground electrode 101, Zg, the previous equation simplifies to: is =Vs/Zs. Equivalently, it can be said that Vs and Ze become a Norton equivalent current source having a current output equal to Vs/Zs and an output impedance of Zs. The test current is then causes a corresponding voltage drop across the channel electrode 102, which is measured by the amplifier 104. Therefore, Vout=Vbody+is*Ze.

In some embodiments, a reference amplifier 118 has a signal input that is coupled to the subject's body through reference electrode 116 having impedance Zr for isolating the potential difference across the channel electrode 102 that is caused by the flow of the test current is through the channel electrode 102 without the additional voltage drop caused by the ground electrode's 101 impedance Zr.

Since no current flows in to the input of the reference amplifier 118, whereby there is no appreciable voltage drop across Zr, the reference amplifier measures Vbody directly (e.g., Vref=Vbody). A second stage differential circuit can be used to subtract Vout from the Vbody for further signal conditioning and digitization. This allows for a direct measurement of the quantity is*Ze, irrespective of the impedance Zg of the ground electrode 101.

To determine the magnitude and phase of Is (and therefore also Vs and Zs) for determining the actual impedance of the channel electrode 102, Ze, a calibration process is normally needed. The values for any given implementation can be easily calibrated by inserting known impedances for Ze on the test bench and recording the output voltage Vout. Once the calibrated value for the test current Is is obtained, both the magnitude and phase of the channel electrode's 102 impedance Ze can be calculated by using the calibrated value for is to solve the equation Ze=(Vout-Vbody)/Is, where each of the quantities are complex numbers. Note: in some applications where only an approximate measurement of electrode contact (e.g., 'lead-on', 'lead-off'), the calculations can be conducted solely in the magnitude domain.

In many applications, the stimulation waveform output by the AC supply 108 will be cyclical (e.g., sine, square, triangular) at an approximately fixed frequency. Setting the frequency higher than that of the physiological signal bandwidth allows for simultaneous, real-time operation of both normal recording as well as impedance measurements, since the higher frequency impedance check signal can be simply low-passed or notched out from the lower frequency biopotential signal. However, the downside is that the measurement technique samples only the channel electrode's 102 impedance Zg at a fixed frequency. In applications where a full impedance spectroscopy is desired, alternative stimulation waveforms may be applied to the AC supply 108 such that an impulse, step, sweep or other test current waveforms with spectral content at multiple frequencies is generated through the conductive element 110. However, such waveforms may necessarily interrupt normal physiological recording.

The modulation of the amplifier 104 by the signal provided by the AC supply 108 goes against conventional practice, which teaches that an amplifier must have a quiet, DC power source to minimize noise and maximize stability. However, modern integrated amplifiers now possess extremely high power supply rejection ratios (PSRR), which greatly relaxes the requirement for a 'quiet' power source. Thus an amplifier with a non-zero PSRR will reject the influence of the AC supply 108 on its operation, provided that the negative extent of the signal from the DC biased AC supply 106, 108 does not prevent the amplifier 104 from functioning normally.

Figure 2:
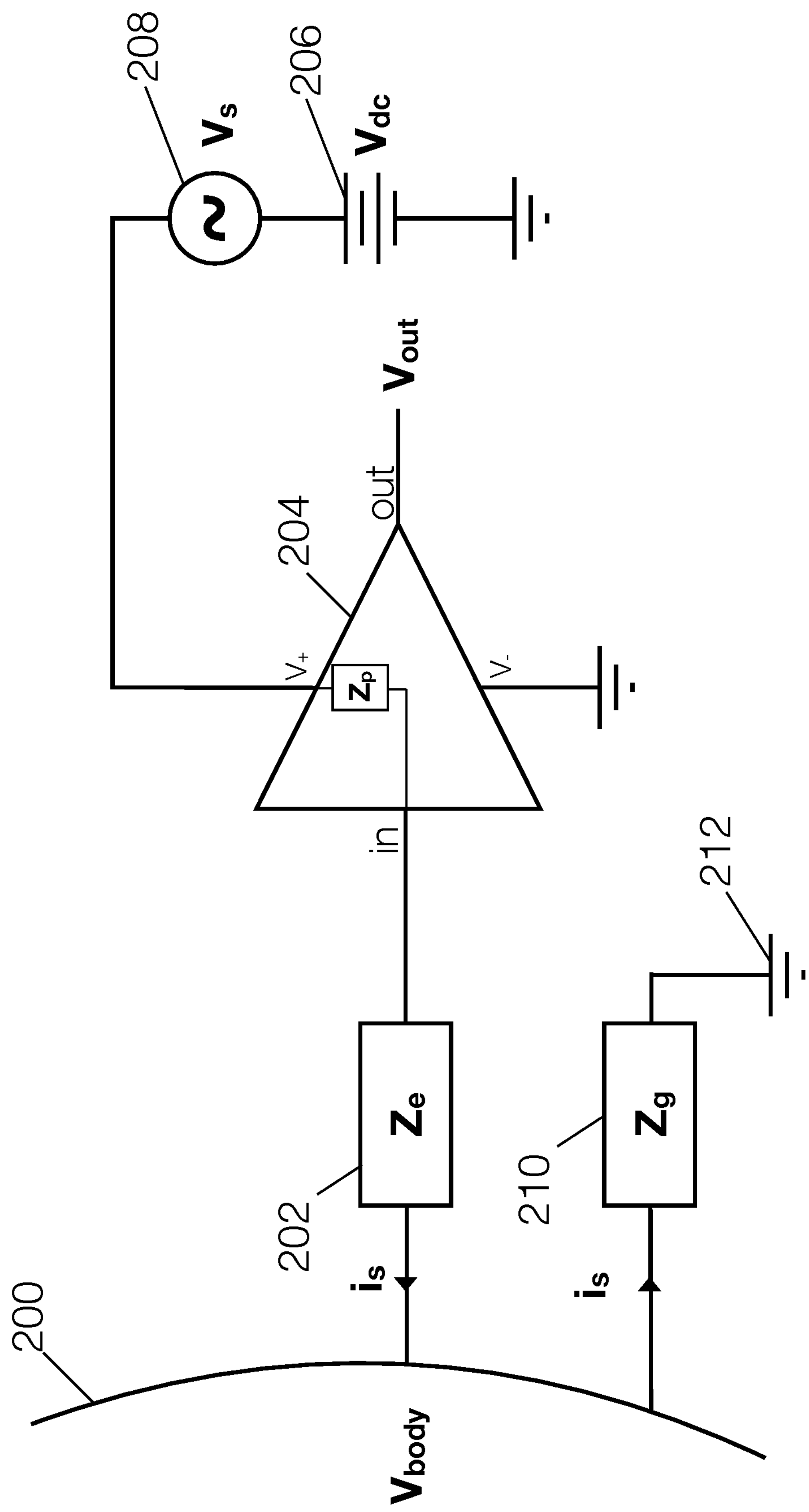
FIG. 2 is a schematic diagram showing a second exemplary embodiment of the impedance measurement circuit of the invention wherein the conductive element is a parasitic element included within the amplifier.

Reduction in the amount of necessary components can be accomplished with the exemplary embodiment shown in FIG. 2, which includes an amplifier 204 and a DC biased AC power supply 206, 208 for providing an AC time varying test current is. The circuit operates in a substantially identical manner as the embodiment shown in FIG. 1. Except, in lieu of the discrete conductive element 110 in the embodiment of FIG. 1, the function of conductive element 110 is provided by a parasitic impedance Zp within the amplifier 204 coupled between the power supply 206, 208 and the signal input of the amplifier 204 for generating the test current is that is applied to a channel electrode 202 that is coupled between the subject's body 200 and the signal input of the amplifier 204. The parasitic conductive element Zp is normally formed by the normal capacitive and resistive leakage structures between the amplifier's 204 input terminal and power terminal.

As before, ground electrode Zg is coupled between the subject's body 200 and circuit ground 212. Although not shown therein, the embodiment of FIG. 2 preferably also includes a reference amplifier (such as the reference amplifier 118 shown in FIG. 1), which has a signal input coupled to the subject's body through an impedance for isolating the potential difference across the channel electrode 202 that is caused by the flow of the test current is through the channel electrode 202 from being influenced by any grounded electrodes in the system.

A major advantage of the embodiment in FIG. 2 is that it achieves the maximum possible input impedance, which is a key requirement for many physiological sensing systems, especially ones involving the use of dry electrodes. Using the inherent parasitic impedance Zp at the amplifier's input avoids the use of extraneous components which will necessarily degrade the input impedance of the system. Advantageously, Zp, is normally a small capacitor in the high-input impedance amplifiers used in biopotential recordings and therefore block potentially harmful DC currents, as previously discussed.

Many possible variations exist. Other embodiments may modulate both power supply terminals of the amplifier 104, 204 for a fully symmetric current flow through a resistive element. Other embodiments may include different compositions of the conductive elements (resistor, capacitor, inductor or any arbitrary combination) to best suit the frequency and expected electrode impedance characteristics of the application. In essence, modulating the power supply terminal of the amplifier virtually eliminates extra wiring and components per electrode channel, which is especially advantageous for multi-channel physiological sensing systems where an amplifier is coupled to each channel electrode. As a result, the invention allows for the realization of multiple active channel electrodes to be placed on the body, where only three wires are necessary: power, signal and ground, since all of the impedance check control is multiplexed with the power line.

In still other embodiments, the various aspects of the different embodiments described herein are combined with one another to the extent that they are not incompatible with each other.

The advantages specifically stated herein do not necessarily apply to every conceivable embodiment of the invention. Further, such stated advantages of the invention are only examples and should not be construed as the only advantages of the invention.

While the above description contains many specificities, these should not be construed as being necessarily required for use of the invention or as limitations on the scope of the invention, but rather as examples of the embodiments described herein. Other variations are possible and the scope of the invention should be determined not by the embodiments described herein but rather by the claims and their legal equivalents.

The invention claimed is:

1. A biopotential-physiological-phenomena sensing system, comprising:
- an impedance measurement circuit that is configured for application to a subject's body for measuring the impedance of a channel electrode that is applied to the subject's body for sensing a physiological phenomenon, including:
- an amplifier having a signal input coupled to the channel electrode that is configured for application to the subject's body and a signal output for providing an output voltage that is representative of a voltage provided at the signal input in accordance with an amplification of the amplifier;
- a DC-biased power supply with an AC component connected to a power supply terminal of said amplifier;
- a conductive element coupled between the power supply terminal and the signal input of the amplifier;
- wherein the AC component of said power supply generates and modulates a known test current from the conductive element and thence through said channel electrode that is applied to the subject's body to produce an output voltage from the amplifier that is representative of a voltage provided at the signal input in accordance with an amplification of the amplifier.

2. The impedance measurement system according to claim 1, wherein the conductive element is a discrete conductive element.

3. The impedance measurement system according to claim 2, wherein the conductive element comprises a capacitor for blocking the flow of DC current.

4. The impedance measurement system according to claim 1, wherein the conductive element is a parasitic element within the amplifier coupled between the power supply and the input of the amplifier for generating the test current applied to the channel electrode.

5. The impedance measurement system according to claim 1, further comprising:
- a DC amplifier configured for application to the subject's body through an impedance for isolating the potential difference across the channel electrode that is caused by the flow of the test current through the channel electrode from being influenced by a grounded electrode in the system.

6. A biopotential-physiological-phenomena sensing system comprising:
- multiple measurement channels respectively including a channel electrode that is configured for application to a subject's body for sensing a physiological phenomenon,
- a plurality of impedance measurement circuits for respectively measuring the impedance of the channel electrode in at least some of the measurement channels, wherein each individual impedance measurement circuit includes:

an amplifier having an input coupled to a channel electrode that is configured for application to the subject's body and a signal output that is representative of voltage provided at the signal input in accordance with an amplification of the amplifier;

a DC-biased power supply with an AC component connected to a power supply terminal of the amplifier;

a conductive element coupled between the power supply and the signal input of the amplifier; and at least one grounded electrode;

wherein the AC component of said power supply generates and modulates a known test current through said conductive element and thence from the signal input of the amplifier to the channel electrode that is applied to the subject's body to produce an output voltage form the amplifier that is representative of a voltage provided at the signal input in accordance with an amplification of the amplifier.

7. The impedance measurement system according to claim 6, wherein the power supply in the measurement circuit of at least one of the individual measurement channels is shared by at least one of the measurement circuits of the other individual measurement channels.

* * * * *